United States Patent
Enssle et al.

(10) Patent No.: US 10,216,175 B2
(45) Date of Patent: Feb. 26, 2019

(54) CONVEYORS INCLUDING SENSORS FOR DETECTING ERROR CONDITIONS ASSOCIATED WITH PRODUCTS TRAVELING ON THE CONVEYORS

(71) Applicant: Walmart Apollo, LLC, Bentonville, AR (US)

(72) Inventors: Benjamin D. Enssle, Bella Vista, AR (US); Cristy C. Brooks, Cassville, MO (US); David C. Winkle, Bella Vista, AR (US); Greg A. Bryan, Centerton, AR (US); Todd D. Mattingly, Bentonville, AR (US)

(73) Assignee: Walmart Apollo, LLC, Bentonville, AR (US)

( * ) Notice: Subject to any disclaimer, the term of this patent is extended or adjusted under 35 U.S.C. 154(b) by 0 days.

(21) Appl. No.: 15/882,692

(22) Filed: Jan. 29, 2018

(65) Prior Publication Data
US 2018/0224837 A1 Aug. 9, 2018

Related U.S. Application Data

(60) Provisional application No. 62/455,121, filed on Feb. 6, 2017.

(51) Int. Cl.
*G05B 19/418* (2006.01)
*G06Q 10/08* (2012.01)
(Continued)

(52) U.S. Cl.
CPC ....... *G05B 19/41875* (2013.01); *B65G 47/50* (2013.01); *G01N 21/95607* (2013.01);
(Continued)

(58) Field of Classification Search
CPC .......... G05B 19/41875; G05B 19/4183; G05B 19/4189; B65G 47/50; G01N 21/95607; G06Q 10/087
See application file for complete search history.

(56) References Cited

U.S. PATENT DOCUMENTS 4,672,553 A 6/1987 Goldberg
5,969,339 A 10/1999 McMurray
(Continued)

FOREIGN PATENT DOCUMENTS

EP 1511680 3/2005
JP 2006508003 3/2006

OTHER PUBLICATIONS

PCT; App. No. PCT/US2018/014971; International Search Report and Written Opinion dated Apr. 4, 2018.

*Primary Examiner* — Bryan Bui
(74) *Attorney, Agent, or Firm* — Fitch, Even, Tabin & Flannery LLP (57) ABSTRACT

In some embodiments, methods and systems are provided that include interconnected conveyors including multiple sensors configured to detect identifying characteristics and physical characteristics of the products traveling on the conveyors. The product-associated information that is detected by the sensors is analyzed relative to predefined product-associated identifying characteristics and physical characteristics stored in a database, and an error signal is generated if the actual, sensor-obtained product identifying characteristics and/or physical characteristics, do not correspond to the predefined, database-stored product identifying characteristics and/or physical characteristics.

18 Claims, 3 Drawing Sheets

(51) Int. Cl.
*B65G 47/50* (2006.01)
*G01N 21/956* (2006.01)
*G06F 17/30* (2006.01)

(52) U.S. Cl.
CPC ..... *G05B 19/4183* (2013.01); *G05B 19/4189* (2013.01); *G06F 17/30522* (2013.01); *G06Q 10/0875* (2013.01); *G06F 17/30598* (2013.01)

(56) References Cited

U.S. PATENT DOCUMENTS

| | | |
|---|---|---|
| 6,104,966 A | 8/2000 | Haagensen |
| 7,816,617 B2 | 10/2010 | Bennett |
| 8,284,993 B2 | 10/2012 | Taylor |
| 9,365,357 B2 | 6/2016 | Ghezal |
| 10,008,078 B2 * | 6/2018 | Kotula ................ G08B 3/10 |
| 2008/0236996 A1 | 10/2008 | Bausenwein |
| 2015/0028098 A1 | 1/2015 | Kleinikkink |
| 2016/0260161 A1 * | 9/2016 | Atchley ................ E01H 5/12 |
| 2016/0342917 A1 | 11/2016 | Surapaneni |
| 2017/0021499 A1 | 1/2017 | Wellman |

\* cited by examiner

CONVEYORS INCLUDING SENSORS FOR DETECTING ERROR CONDITIONS ASSOCIATED WITH PRODUCTS TRAVELING ON THE CONVEYORS

CROSS-REFERENCE TO RELATED APPLICATIONS

This application claims the benefit of U.S. Provisional Application No. 62/455,121, filed Feb. 6, 2017, which is incorporated herein by reference in its entirety.

TECHNICAL FIELD

This invention relates generally to sorting products using conveyors and, in particular, to systems and methods for sorting products using conveyors having multiple sensors.

BACKGROUND

Retailers routinely transport products within product distribution facilities using conveyor systems. For example, products and/or packages are routinely transported from a product packaging or sorting area via conveyors to a product loading area (e.g., into a delivery vehicle). It is not uncommon for products traveling on such conveyors and destined for delivery to a consumer to be damaged, for example, as a result of some manipulation by a worker at the product distribution facility, or as a result of being defective, or as a result of not being maintained at its proper storage/transportation temperature. If such anomalies in the products are not detected prior to such defective and/or damaged products being loaded into delivery vehicles and delivered to consumers, the consumers not only become unhappy with the retailer and may not order from the retailer again, but also return the defective and/or damaged products back to the retailer, thereby increasing the retailer's cost and reducing the retailer's profits.

BRIEF DESCRIPTION OF THE DRAWINGS

Disclosed herein are embodiments of systems, apparatuses, and methods pertaining to sorting and tracking products at a product distribution facility includes a plurality of interconnected conveyors configured to move the products. This description includes drawings, wherein.

Elements in the figures are illustrated for simplicity and clarity and have not been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments of the present invention. Certain actions and/or steps may be described or depicted in a particular order of occurrence while those skilled in the art will understand that such specificity with respect to sequence is not actually required. The terms and expressions used herein have the ordinary technical meaning as is accorded to such terms and expressions by persons skilled in the technical field as set forth above except where different specific meanings have otherwise been set forth herein.

DETAILED DESCRIPTION

The following description is not to be taken in a limiting sense, but is made merely for the purpose of describing the general principles of exemplary embodiments. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

Generally speaking, pursuant to various embodiments, systems and methods are provided for sorting and tracking products at a product distribution facility.

In one embodiment, a system for sorting and tracking products at a product distribution facility includes a plurality of interconnected conveyors configured to move the products, a first sensor positioned proximate a product advancement surface of at least one of the conveyors and configured to detect at least one identifying characteristic of at least one product moving on the product advancement surface, and a second sensor positioned proximate the product advancement surface and configured to detect at least one physical characteristic of the at least one product moving on the product advancement surface. The system further includes an electronic database storing inventory management data including: data indicating predefined identifying characteristic and physical characteristic information associated with the at least one product, the predefined identifying characteristic and physical characteristic information corresponding to the at least one product when in a new condition and undamaged; data indicating actual identifying characteristic information associated with the at least one product, the actual identifying characteristic information corresponding to the at least one product when detected by the first sensor during movement of the at least one product along the product advancement surface; and data indicating actual physical characteristic information associated with the at least one product, the actual physical characteristic information corresponding to the at least one product when detected by the second sensor during movement of the at least one product along the product advancement surface. The system further includes a processor-based electronic inventory management device in communication with the first and second sensors and the electronic database. The electronic inventory management device is configured obtain the inventory management data stored in the electronic database and, based on the obtained inventory management data, to: compare the data indicating the actual identifying characteristic information associated with the at least one product detected by the first sensor during movement on the product advancement surface to the data indicating the predefined identifying characteristic information associated with the at least one product in order to determine an identity of the at least one product detected by the first sensor; compare the data indicating the actual physical characteristic information associated with the at least one product detected by the second sensor during movement on the product advancement surface to the data indicating the predefined physical characteristic information associated with the at least one product in order to verify that the identity of the at least one product and that the condition of the at least one product detected by the second sensor is new and undamaged; and redirect movement of the at least one product detected by the first and second sensors on the product advancement surface of the at least one of the conveyors in response to a determination, by the electronic inventory management device, that a verification of the identity of the at least one product failed or that the at least one product is not in a new condition or is in a damaged condition.

In another embodiment, a method for sorting and tracking products at a product distribution facility includes: providing a plurality of interconnected conveyors configured to move the products; providing a first sensor positioned proximate a product advancement surface of at least one of the conveyors and configured to detect at least one identifying characteristic of at least one product moving on the product advancement surface; providing a second sensor positioned proximate the product advancement surface and configured to detect at least one physical characteristic of the at least one product moving on the product advancement surface; providing an electronic database storing inventory management data including: data indicating predefined identifying characteristic and physical characteristic information associated with the at least one product, the predefined identifying characteristic and physical characteristic information corresponding to the at least one product when in a new condition and undamaged; and data indicating actual identifying characteristic information associated with the at least one product, the actual identifying characteristic information corresponding to the at least one product when detected by the first sensor during movement of the at least one product along the product advancement surface; data indicating actual physical characteristic information associated with the at least one product, the actual physical characteristic information corresponding to the at least one product when detected by the second sensor during movement of the at least one product along the product advancement surface; and providing a processor-based electronic inventory management device in communication with the first and second sensors and the electronic database, the electronic inventory management device being configured obtain the inventory management data stored in the electronic database and, based on the obtained inventory management data, to: compare the data indicating the actual identifying characteristic information associated with the at least one product detected by the first sensor during movement on the product advancement surface to the data indicating the predefined identifying characteristic information associated with the at least one product in order to determine an identity of the at least one product detected by the first sensor; compare the data indicating the actual physical characteristic information associated with the at least one product detected by the second sensor during movement on the product advancement surface to the data indicating the predefined physical characteristic information associated with the at least one product in order to verify that the identity of the at least one product and that the condition of the at least one product detected by the second sensor is new and undamaged; and redirect movement of the at least one product detected by the first and second sensors on the product advancement surface of the at least one of the conveyors in response to a determination, by the electronic inventory management device, that a verification of the identity of the at least one product failed or that the is not in a new condition or is in a damaged condition.

Figure 1:
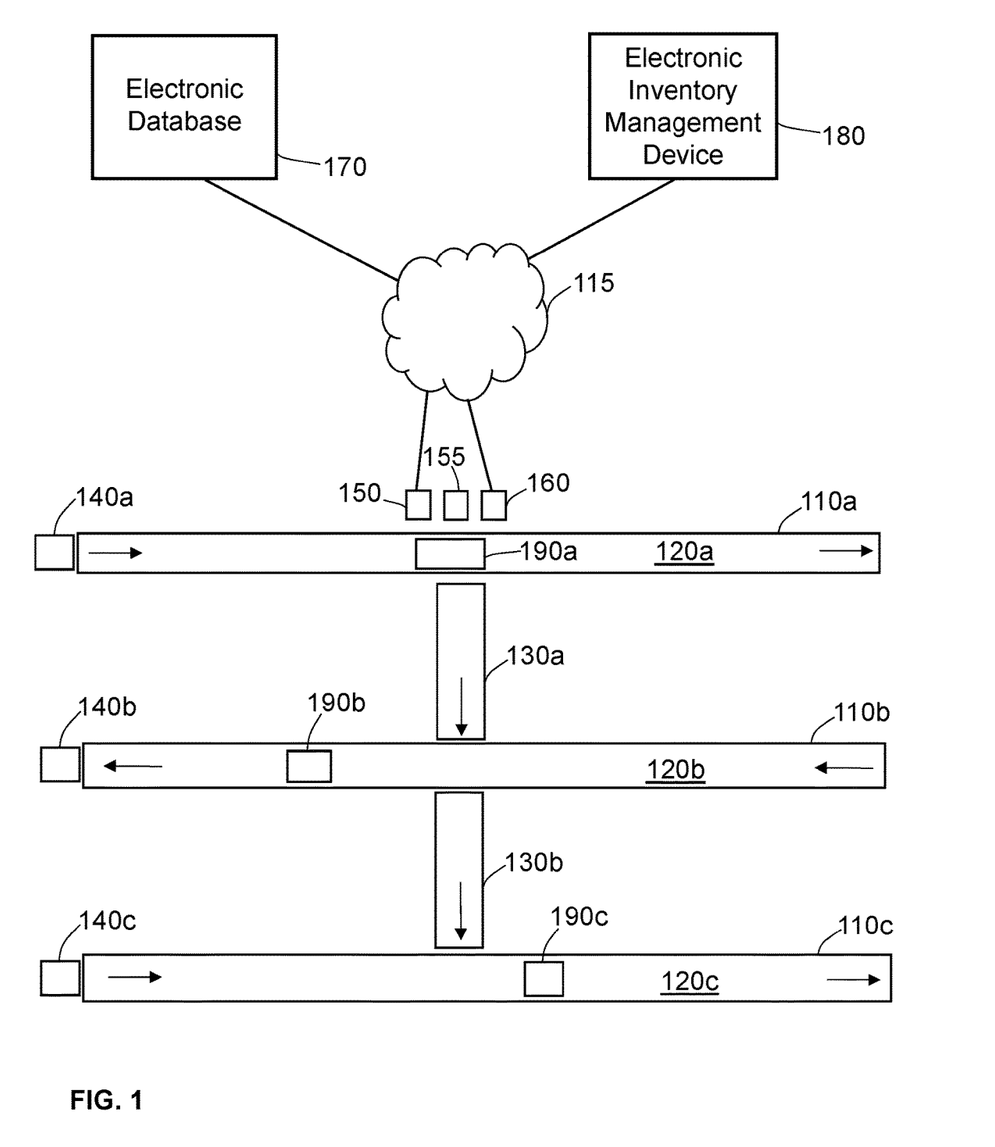
FIG. 1 is a diagram of a system of sorting and tracking products at a product distribution facility includes a plurality of interconnected conveyors configured to move the products in accordance with some embodiments.

FIG. 1 shows an embodiment of a system 100 for sorting and tracking products 190. The exemplary system 100 shown in FIG. 1 for simplicity of illustration with only three conveyors 110a-c and three products 190a-190c thereon, but it will be appreciated that the system 100 may include less conveyors (e.g., 1 or 2), or more conveyors (e.g., from 4, 10, 20, 30, 50, 100, or more) depending on the size of the product distribution facility where the conveyor system 100 is installed, and depending on the number of products 190 passing through the system 100. By the same token, while each conveyor 110a-110c is illustrated in FIG. 1 as having one product 190a-190c thereon, respectively, it will be appreciated that each of the conveyors 110a-110c may concurrently transport more than one product 190a-190c (e.g., dozens and/or hundreds of products, depending on the length of the conveyor). In addition, while this application refers to products 190a-190c and the sorting of products 190a-190c, it will be appreciated that the conveyor system 100 may be used to transport products that are retained in packages, boxes, and/or totes, and/or loose products that are not packaged. Further, the size of the products 190a-190c in FIG. 1 has been shown by way of example only, and it will be appreciated that the conveyors may transport many different products 190a-190c having many different sizes and shapes.

The exemplary conveyors 110a-110c of FIG. 1 can be horizontally adjacent or vertically stacked relative to one another. The conveyors 110a-110c each have a product advancement surface 120a-120c configured to move one or more products 190a-190c in one or more directions indicated by the arrows. The product advancement surface 120a-120c of the conveyors 110a-110c may be comprised of a single conveyor belt surface (horizontal (as shown) or inclined), or may be instead comprised of a series of two or more independently movable conveyor belt surfaces (horizontal or inclined). The conveyors 110a-110c may be belt conveyors, chain conveyors, or the like and may have a continuous, uninterrupted product advancement surface 120a-120c, or may have a product advancement surface 120a-120c that includes one or more interruptions at the transitions between the distinct conveyor surfaces.

In the embodiment shown in FIG. 1, the system 100 further includes transfer conveyors 130a and 130b interconnecting the conveyors 110a-110c and providing multiple transfer nodes where the products 190a-190c may be transferred between the conveyors 110a-110c. Similarly to the product advancement surfaces 120a-120c of conveyors 110a-110c, the transfer conveyors 130a-130b may be independently movable relative to one another. As such, either one of the transfer conveyors 130a-130b may be stopped while the other one is permitted to move. It will be appreciated that each of the transfer conveyors 130a-130b may be movable in one direction only (e.g., to permit for product transfer from conveyor 110a to conveyor 110b, but not vice versa), or may be movable in two directions (e.g., to permit for product transfer from conveyor 110a to conveyor 110b and from conveyor 110b to conveyor 110a).

In the system 100 shown in FIG. 1, the transfer conveyors 130a-130b are shown as being oriented in a direction perpendicular to the respective product advancement surfaces 120a-120c that transfer conveyors 130a-130b interconnect. However, it will be appreciated that the transfer conveyors 130a-130b may be oriented in a direction that is not perpendicular (e.g., at a 30 degree, 60 degree, 120 degree, or 150 degree angle) relative to their respective product advancement surfaces 120a-120c. Also, while conveyors 110a and 110b are interconnected by one transfer conveyor 130a and conveyors 110b and 110c are interconnected by one transfer conveyor 130b, it will be appreciated that each conveyor 110a-110c may be connected by more than one transfer conveyor to more than one other conveyors, and that each of the conveyors 110a-110c may include two or more (e.g., 5, 10, 25, 50, 100, or more) transfer conveyors 130a-130b coupled thereto, depending on the length of the conveyors 110a-110c, and the throughput needs of a product distribution facility where system 100 is implemented and the size of the system 100.

In order to effectuate the directional movement of the product advancement surface 120a-120c of the conveyors 110a-110c and the movement of products 190a-c thereon, the exemplary system 100 illustrated in FIG. 1 includes a conveyor control unit 140a-140c coupled (e.g., electrically) to each respective conveyor 110a-110c. The conveyor control units 140a-140c can be located at or near the conveyors 110a-110c as shown in FIG. 1, or may be built into and/or on the conveyors 110a-110c. In some embodiments, the conveyor control units 140a-140c are configured to receive a signal from an electronic inventory management device 180 (which will be described in more detail below) and, in response to receipt of such a signal, to either cause their respective product advancement surface 120a-120c (and/or their respective transfer conveyor 130a-130c) to move in the direction shown by directional arrows in FIG. 1 (or in an opposite direction), or to stop. It will be appreciated that each of the transfer conveyors 130a-130c, instead of being controlled by the conveyor control units 140a-140c, can have their own respective conveyor control units coupled thereto.

The exemplary system 100 shown in FIG. 1 includes a first sensor 150 positioned proximate the product advancement surface 120a of the conveyor 110a. In some aspects, the sensor 150 is configured to detect at least one identifying characteristic of a product 190a moving on the product advancement surface 120a. According to some embodiments, the sensor 150 can include one or more sensors including but not limited to a motion-detecting sensor, a photo sensor, a radio frequency identification (RFID) sensor, an optical sensor, a barcode sensor, and a digital camera sensor. The system 100 also includes a second sensor 155 positioned proximate the product advancement surface 120a of the conveyor 110a. In some aspects, the sensor 155 is configured to detect at least one physical characteristic of the product 190a moving on the product advancement surface 120a. According to some embodiments, the sensor 155 can include one or more sensors including but not limited to a weight sensor, a volumetric sensor, size sensor, a 3-D sensor, a gas/chemical sensor, an infrared sensor, a thermal sensor, or the like.

In some embodiments, the system 100 includes a third sensor 160 positioned proximate the product advancement surface 120a of the conveyor 110a and configured to detect the presence and/or location of the product 190a moving on the product advancement surface 120a of conveyor 110a. According to some embodiments, the sensor 160 can include one or more sensors including but not limited to a motion-detecting sensor, physical contact sensor, barcode-scanning sensor, RFID-detecting sensor, digital camera sensor, or the like.

In some embodiments, the sensors 150 and/or 160 are configured to scan identifying indicia located on the product 190a or on the packaging containing the product 190a. The identifying indicia on the product 190a that may be scanned by the sensor 160 may include, but is not limited to: two dimensional barcode, RFID, near field communication (NFC) identifiers, ultra-wideband (UWB) identifiers, Bluetooth identifiers, images, or other such optically readable, radio frequency detectable or other such code, or combination of such codes.

In some aspects, a product identifying characteristic-detecting sensor 150 in the form of a camera provides for image analysis of the product 190a, text recognition on the product 190a (e.g., product name), and/or pattern recognition on the product 190a (e.g., color pattern or barcode pattern) as the product 190a is moving on the product advancement surface 120a. For example, a camera-based sensor 150 monitoring a product 190a that is a cardboard case (normally having a uniform light brown color pattern) moving along the product advancement surface 120a can acquire a visual pf the product 190a (i.e., cardboard case) and detect a darker patch in the cardboard case, which, when transmitted to the electronic inventory management device 180, can be interpreted by the control circuit 210 of the electronic inventory management device 180 as a hole in the cardboard case, which can lead to a redirection of the product 190 from its initial route on the conveyor 110a either to product sorting or disposal.

In some aspects, a tolerated damage or anomaly threshold can be preprogrammed into the control circuit 210 of the electronic inventory management device 180. Such a threshold, for example, can be a percentage of area of the cardboard case with unexpected (i.e., darker patch) color. In other words, if one or more surfaces of the product 190a (or product packaging) are detected to have an anomaly or mismatch in more than a tolerated preset percentage (e.g., 5%, 10%, 20%) of its surface area, the control circuit 210 is programmed to divert the product 190a from its original route along the product advancement surface 120a of conveyor 110a to a different conveyor (e.g., 110b) for transporting the product 190 back to a product sorting/packaging area. In one aspect, such a redirection of the product 190a is accompanied by an alert signal transmitted from the electronic inventory management device 180 to a hand-held electronic device of a worker at the product distribution facility. In some aspects, a camera-based sensor 150 captures an image of a product 190 that visually indicates a liquid spill on the product advancement surface 120a, a granule or particle presence on the product advancement surface 120a, a product body deformation such as an ice cream melting, for example, (in some aspects, by more than a tolerated deformation percentage (e.g., 10%, 20%, etc.) threshold), or loose items that fell out of their original packaging.

In certain implementations, the camera-based sensor 150 is configured to capture an image of the product 190 traveling on the product advancement surface 120a and to compress the captured image prior to transmitting the compressed image to the electronic database 170 for storage and later analysis by the control circuit 210 of the inventory management device 180. This image compression by the camera-based sensor 150 advantageously reduces the storage requirements of the electronic database 170 (as compared to capturing and transmitting full-size images), and advantageously reduces the processing power required of the control circuit 210 to process the compressed image (as compared to the full-size image) when attempting to detect any physical characteristic anomalies of the product 190a-

190c based on processing the image captured by the camera-based sensor 150 and stored in the electronic database 170.

In one aspect, a product physical characteristic-detecting sensor 155 is a weight sensor in the form of a plate or a roller positioned under the product advancement surface 120a that provides for the measurement of the weight of the product 190a as the product 190a passes over the weight sensor. In one aspect, the weight sensor 155 is in the form of one or more piezoelectric sensors embedded into the product advancement surface 120a of the conveyor 110a. In some embodiments, a weight of a product 190a detected by the sensor 155 is transmitted by the sensor 155 to the electronic inventory management device 180 and correlated by the electronic inventory management device 180 to a predefined weight of the product 190 when the product 190a is new and undamaged (which predefined weight is obtained from the electronic database 170). If the comparison, by the control circuit 210 of the electronic inventory management device 180, of the actual weight of the product 190a (or of multiple units of product 190a packaged in a case) that is measured by the sensor 155 to the predefined weight of the product 190a (or multiple units of the product 190a packaged in a case) when the product 190a is new and undamaged indicates a discrepancy that exceeds a certain tolerated threshold (e.g., 5%, 10%, etc.) between the two weights, an error condition is triggered by the control circuit 210 of the electronic inventory management device 180, which, in some embodiments, results in the redirection of the product 190a from conveyor 110a to conveyor 110b.

In one aspect, a product physical characteristic-detecting sensor 155 is an infrared and/or a thermal sensor that measures the temperature of the product 190a and/or insulation integrity of the packaging of the product 190a as the product 190a is moving on the product advancement surface 120a. In some embodiments, a temperature of a product 190 (e.g., a temperature-sensitive perishable product) detected by the sensor 155 is transmitted by the sensor 155 to the electronic inventory management device and correlated by the electronic inventory management device 180 to a predefined temperature (e.g., 32° F.) required for the product 190a to maintain its desired texture or freshness (which predefined temperature is obtained from the electronic database 170). If the comparison, by the control circuit 210 of the electronic inventory management device 180, of the actual temperature of the product 190a that is measured by the sensor 155 to the predefined temperature of the product 190a when the product 190a is at its proper storage temperature indicates a discrepancy that exceeds a certain tolerated threshold (e.g., 1° F., 2° F., 3° F., 5° F., 10° F., etc.) between the two temperatures, an error condition is triggered by the control circuit 210 of the electronic inventory management device 180.

In one embodiment, the product physical characteristic-detecting sensor 155 is a 3D scanner or sensor configured to detect and/or measure the shapes and/or dimensions of the product 190a moving on the product advancement surface 120a and/or distances between the products moving on the product advancement surface 120a. In one aspect, shape or size of a product 190a detected by the 3-D sensor 155 is transmitted by the sensor 155 to the electronic inventory management device 180 and correlated by the electronic inventory management device 180 to a predefined shape or size of the product 190 when the product 190a is new and undamaged (which predefined shape or size is obtained from the electronic database 170). If the comparison, by the control circuit 210 of the electronic inventory management device 180, of the actual shape or size of the product 190a (or of multiple units of product 190a packaged in a case) that is measured by the sensor 155 to the predefined shape or size of the product 190a (or multiple units of the product 190a packaged in a case) when the product 190a is new and undamaged indicates a discrepancy that exceeds a certain tolerated threshold (e.g., 5%, 10%, etc.) between the two shapes or sizes, an error condition is triggered by the control circuit 210 of the electronic inventory management device 180, which, in some instances, results in the redirection of the product 190a from conveyor 110a to conveyor 110b.

In one embodiment, the product physical characteristic-detecting sensor 155 is a chemical or gas sensor configured to detect a gas (e.g., ethylene gas, methane, etc.) or chemical odor released by the product 190 (e.g., seafood, meat, dairy, etc.) when the product 190 is spoiled. For example, in some aspects, if an analysis, by the control circuit 210 of the electronic inventory management device 180, of the gas detected by the sensor 155 exceeds a certain tolerated threshold for that gas (e.g., 10 ppb, 30 ppb, 50 ppb, 100 ppb, etc.), an error condition is triggered by the control circuit 210 of the electronic inventory management device 180, which, in some cases, results in the redirection of the product 190a from conveyor 110a to conveyor 110b.

It will be appreciated that in some embodiments, equivalents of sensors, 150a-150c can be positioned proximate the product advancement surfaces 120b-120c, which has not been shown in FIG. 1 for ease of illustration. In addition, while FIG. 1 shows the sensors 150a-150c as being positioned adjacent and above the conveyor 110a, it will be appreciated that the sensors 150a-b may be positioned below, and on one or both sides of the conveyor 110a. In addition, the locations of the sensors 150a-150c relative to the conveyor 110a in FIG. 1 are by way of example only, and the sensors 150a-150c may be placed at different locations, as well as multiple repeating locations, along the product advancement surface 120a of conveyor 110a. Furthermore, it will be appreciated that one or more of the sensors 150a-150c can be physically incorporated (e.g., coupled to, embedded, etc.) into the physical structure of the conveyor 110a and/or product advancement surface 120a.

In the embodiment shown in FIG. 1, the system 100 includes an electronic (inventory management) database 170. In some embodiments, the electronic inventory management device 180 and the electronic database 170 may be implemented as two separate physical devices in the same physical location as the conveyors 110a-110c of system 100 as shown in FIG. 1. It will be appreciated, however, that the electronic inventory management device 180 and the electronic database 170 may be implemented as a single physical device, and may be located at different locations relative to each other and relative to the conveyors 110a-110c. In some embodiments, the electronic database 170 may be stored, for example, on non-volatile storage media (e.g., a hard drive, flash drive, or removable optical disk) internal or external to the electronic inventory management device 180, or internal or external to computing devices distinct from the electronic inventory management device 180. In some embodiments, the electronic database 170 may be cloud-based.

In some embodiments, the exemplary electronic database 170 of FIG. 1 is configured to store electronic data associated with the products 190a-190c moving on the conveyors 110a-110c and which is acquired by one or more of the sensors 150, 155, and 160. Some exemplary electronic data that may be stored in the electronic database 170 includes but is not limited to: identification of the products 190a-190c (e.g., barcode and/or other identifying indicia); date of purchase of the products 190a-190c (if applicable); price of purchase of the products 190a-190c (if applicable); number of units of the products 190a-190c to be transported via the conveyors 110a-110c; delivery destination pertaining to the products 190a-190c; delivery vehicle loading location and delivery vehicle scheduling information associated with the products 190a-190c; and information (e.g., name, address, payment information, etc.) pertaining to one or more consumers (or other intended recipients) associated with the products 190a-c.

In some configurations, the inventory management data stored by the electronic database 170 includes order information associated with the product 190a moving on the product advancement surface 120a of conveyor 110, for example, when the product 190a is moving on the conveyor 110 at the product distribution facility for the purpose of being transported to a delivery truck to be delivered to the customer who ordered this product 190a. Here, the control circuit 210 of the electronic inventory management device 180 is programmed to obtain the order information associated with the product 190a from the electronic database 170 after the identity (e.g., barcode) and the condition (e.g., new and undamaged) of the product 190 are successfully verified by the control circuit 210, and to determine whether the verified identity of the product 190a moving on the product advancement surface 120a of the conveyor 110a is consistent with the order information associated with the product 190a obtained by the control circuit 210 of the electronic inventory management device 180 from the electronic database 170.

In some embodiments, the inventory management data stored by the electronic database 170 includes but is not limited to: data indicating one or more predefined identifying characteristics associated with the products 190a-190c; data indicating one or more predefined physical characteristic associated with the products 190a-190c; data indicating actual identifying characteristic information associated with the products 190a-190c; and data indicating actual physical characteristic information associated with the products 190a-190c. In some aspects, the predefined identifying characteristic and physical characteristic information each correspond to the products 190a-190c when they are in a new condition and undamaged; the actual identifying characteristic information corresponds to the products 190a-190c when detected by the sensor 150 during movement of the products 190a-c along their respective product advancement surface 120a-120c; and the actual physical characteristic information corresponding to the products 190a-190c when detected by the sensor 155 during movement of the products 190a-190c along their respective product advancement surface 120a-120c.

In some embodiments, the inventory management data stored by the electronic database 170 further includes the error conditions detected by the sensor 155 during a scan of the products 190a-190c. For example, in some aspects, each time the sensor 155 triggers an error signal based on detecting an apparent anomaly in the physical characteristic of the scanned product 190a-190c (e.g., weight, size, shape, temperature, etc.), this error signal is communicated by the sensor 155 to the electronic database 170 for storage. The error signals stored in the electronic database 170 may be used in some implementations as data that provides metrics and trends that may be used (e.g., by supervisory personnel) to analyze the quality of the work product of the workers that are tasked with loading the products 190a-190c onto the conveyors 110a-110c.

For example, a statistically significant high number of error signals associated with the tasks performed by a given worker as compared to the other workers working assigned to the conveyors 110a-110c may be indicative that this worker is not using appropriate care when handling the products 190a-190c during the loading of the products 190a-190c onto the conveyors 110a-110c. By the same token, the error signals stored in the electronic database 170 may be used in some implementations as data that provides metrics and trends indicative of the quality of products 190a-190c provided by various manufacturers/distributors/delivery services. For example, a statistically high number of error conditions (e.g., weight anomaly associated with a possible leak, etc.) detected with a given packaged product may be indicative of the poor quality of the packaging by the manufacturer of this product and/or of a lack of care used by the delivery service when transporting this product.

In some embodiments, the inventory management data stored by the electronic database 170 further includes exception handling data reflecting each instance when sensor 155 falsely triggers an error signal indicative that one or more of the scanned products 190a-190c deviates beyond the tolerated threshold from the predefined default physical characteristics of the products 190a-190c associated with the products 190a-190c being in a new and undamaged condition and/or at their desired/required storage temperature. In other words, each time an error condition is detected by the sensor 155 during a scan of the products 190a-190c and a product 190a-190c is diverted from its originally intended travel path along the conveyors 110a-110c, both the error condition and the accompanying travel diversion of the anomaly-associated product 190a-190c are transmitted to and recorded in the electronic database 170.

In some aspects, if a product 190a-190c diverted from its original travel path is determined later on (e.g., at the product loading location, disposal location, etc.) by a worker not to be damaged based on a physical inspection, the worker would then enter exception handling data into the electronic database 170 (e.g., via a hand-held device or a desktop computer). This exception handling data entered by the worker would be associated in the electronic database 170 with the sensor 155 that triggered the error signal, thereby providing the system 100 with exception error handling recordation and metric generation options. In certain aspects, the system 100 is enabled with machine-learning functions associated with exception error handling, where the control circuit of the electronic inventory management device 180 is programmed to determine that a given sensor 155 is faulty based on detecting a statistically significant number of false positive error alerts generated by that sensor 155 with respect to the products 190a-190c that are later contradicted by a physical inspection of the products 190a-190c by the workers.

The exemplary system 100 of FIG. 1 further includes an electronic inventory management device 180 configured to communicate with the conveyor control units 140a-140c, sensors 150, 155, 166, and electronic database 170. The electronic inventory management device 180 may be a stationary or portable electronic device, for example, a desktop computer, a laptop computer, a tablet, a mobile phone, or any other electronic device including a processor-based control circuit (i.e., control unit). In the embodiment of FIG. 1, the electronic inventory management device 180 is configured for data entry and processing as well as for communication with other devices of system 100 via the network 115 which may be a wide-area network (WAN), a local area network (LAN), a personal area network (PAN), a wireless local area network (WLAN), or any other internet or intranet network, or combinations of such networks. The electronic inventory management device 180 may be located at the same physical location as the conveyors 110a-110c and/or the electronic database 170, or may be located at a remote physical location relative to the conveyors 110a-110c and/or the electronic database 170.

Figure 2:
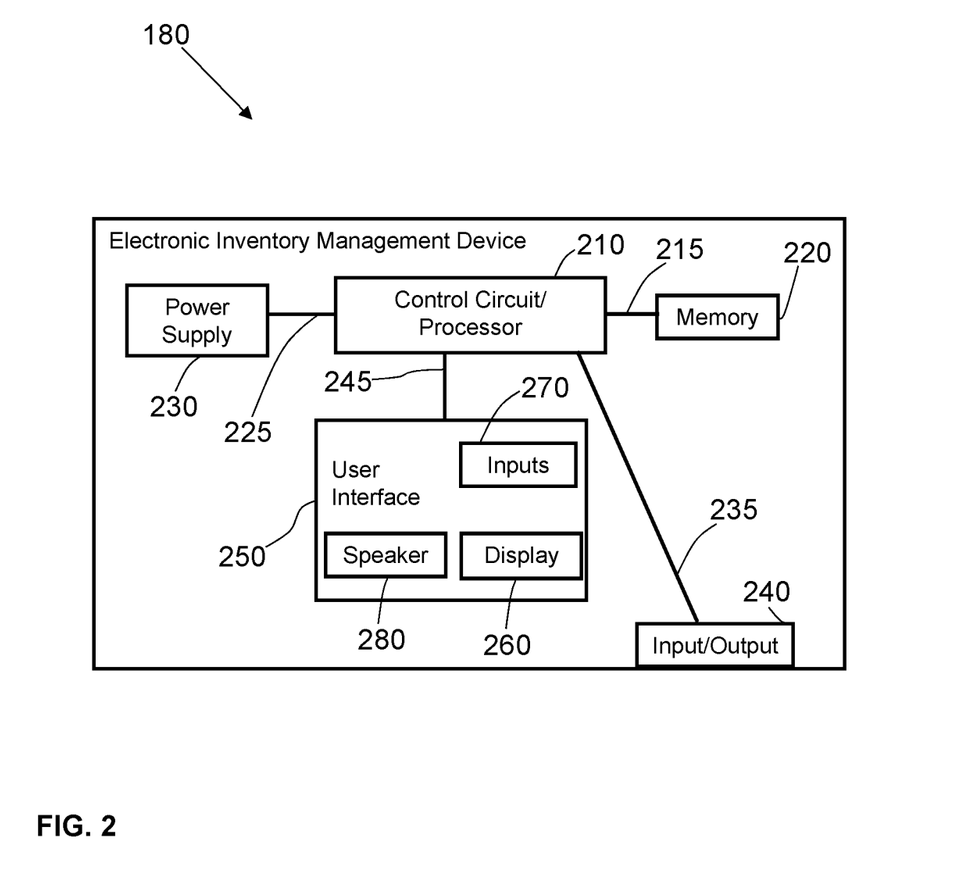
FIG. 2 is a functional diagram of an exemplary electronic inventory management device usable with the system of FIG. 1 in accordance with some embodiments.

With reference to FIG. 2, the electronic inventory management device 180 configured for use with exemplary systems and methods described herein may include a control unit or control circuit 210 including a processor (e.g., a microprocessor or a microcontroller) electrically coupled via a connection 215 to a memory 220 and via a connection 225 to a power supply 230. The control circuit 210 can comprise a fixed-purpose hard-wired platform or can comprise a partially or wholly programmable platform, such as a microcontroller, an application specification integrated circuit, a field programmable gate array, and so on. These architectural options are well known and understood in the art and require no further description here.

This control circuit 210 can be configured (for example, by using corresponding programming stored in the memory 220 as will be well understood by those skilled in the art) to carry out one or more of the steps, actions, and/or functions described herein. In some embodiments, the memory 220 may be integral to the processor-based control circuit 210 or can be physically discrete (in whole or in part) from the control circuit 210 and is configured non-transitorily store the computer instructions that, when executed by the control circuit 210, cause the control circuit 210 to behave as described herein. (As used herein, this reference to "non-transitorily" will be understood to refer to a non-ephemeral state for the stored contents (and hence excludes when the stored contents merely constitute signals or waves) rather than volatility of the storage media itself and hence includes both non-volatile memory (such as read-only memory (ROM)) as well as volatile memory (such as an erasable programmable read-only memory (EPROM))). Accordingly, the memory and/or the control unit may be referred to as a non-transitory medium or non-transitory computer readable medium.

The control circuit 210 of the electronic inventory management device 180 is also electrically coupled via a connection 235 to an input/output 240 that can receive signals from, for example, from the sensors 150, 155, and/or 160, and/or from the conveyor control units 140a-140c (e.g., a signal indicating which product 190a-190c has been transferred from which conveyor 110a-110c and to which conveyor 110a-110c), and/or from the electronic database 170, and/or from another electronic device (e.g., a hand-held electronic device of a worker) over the network 115. The input/output 240 of the electronic inventory management device 180 can also send signals to the conveyor control units 140a-140c indicating which product 190a-190c to transfer from which conveyor 110a-110c and to which conveyor 110a-110c.

The processor-based control circuit 210 of the electronic inventory management device 180 shown in FIG. 2 is electrically coupled via a connection 245 to a user interface 250, which may include a visual display or display screen 260 (e.g., LED screen) and/or button input 270 that provide the user interface 250 with the ability to permit an operator (e.g., worker at a product distribution facility where the system 100 is implemented, or a worker at a remote control center) of the electronic inventory management device 180 to manually control the electronic inventory management device 180 by inputting commands via touch-screen and/or button operation and/or voice commands. The user interface 250 of the electronic inventory management device 120 may also include a speaker 280 that provides audible feedback (e.g., alerts) to the user. Possible commands may, for example, cause the electronic inventory management device 180 to send out a signal to the conveyor control unit 140a-140c of a conveyor 110a-110c in order to cause a product 190a-190c to be transferred from one conveyor (e.g., 110a) to another conveyor (e.g., 110b). For example, such manual control by an operator may be via the user interface 250 of the electronic inventory management device 180, via another electronic device of the operator, or via another user interface and/or switch, and may include an option to override the initial routing for the products 190a-190c on the conveyors 110a-110c preset by the electronic inventory management device 180, and to set new routing for the products 190a-190c (e.g., for which evidence of damage or other unacceptable condition was detected by the sensors 155) on the conveyors 110a-110c. It will be appreciated that the performance of such functions by the processor-based control circuit 210 of the electronic inventory management device 180 is not dependent on a human operator, and that the control circuit 210 may be programmed to perform such functions without a human operator.

In some embodiments, the control circuit 210 of the electronic inventory management device 180 is configured obtain the aforementioned inventory management data stored in the electronic database 170. In some aspects, based on the inventory management data obtained from the electronic database 170 in association with a given product 190a, the control circuit 210 of the electronic inventory management device 180 is programmed to compare the data indicating the actual identifying characteristic information associated with the product 190a detected by the first sensor 150 during movement of the product 190a on the product advancement surface 120a to the data indicating the predefined identifying characteristic information associated with the product 190a in order to determine an identity of the product 190a detected by the first sensor 150. In other aspects, based on the inventory management data obtained from the electronic database 170 in association with a given product 190a, the control circuit 210 of the electronic inventory management device 180 is programmed to compare the data indicating the actual physical characteristic information associated with the product 190a detected by the second sensor 155 during movement of the product 190a on the product advancement surface 120a to the data indicating the predefined physical characteristic information associated with the product 190a in order to verify that the identity and physical condition of the product 190a detected by the second sensor 155 reflect a new and undamaged product 190a.

In some embodiments, the control circuit 210 of the electronic inventory management device 180 is programmed, in response to a determination, by the electronic inventory management device 180, that a verification of the identity of the product 190a failed, or that the product 190a is not in a new condition, or is in a damaged condition, or is not being transported in storage conditions (e.g., suitable temperature) suitable for the product 190a, to transmit an electronic error message to an electronic device of a worker at the product distribution facility. In one aspect, the control circuit 210 of the electronic inventory management device 180 is programmed, in response to a determination, by the electronic inventory management device 180, that a verification of the identity of the product 190a failed, or that the product 190a is not in a new condition, or is in a damaged condition, or is not being transported in storage conditions (e.g., suitable temperature) suitable for the product 190a, to redirect movement of the product 190a detected by the sensors 150, 155 and/or 160 on the product advancement surface 120a of the conveyor 110a.

In some aspects, the control circuit 210 of the electronic inventory management device 180 is programmed to compare actual route information of the product 190a based on detection of the product 190a by the sensor 160 to the predefined route information associated with the product 190a in the electronic database 170 and to redirect movement of the product 190a on the product advancement surface 120a of the conveyor 110 in response to a determination that the actual route of the product 190a moving on the product advancement surface 120a of the conveyor 110a is not consistent with the predefined route information associated with the product 190a that was obtained from the electronic database 170. In one aspect, the control circuit 210 of the electronic inventory management device 180 is programmed, in response to the determination by the control circuit 210 of the electronic inventory management device 180 that the actual route of the product 190a moving on the product advancement surface 120a of the conveyor 110a is inconsistent with the route information associated with the product 190a, to transmit an electronic error message to an electronic device of a worker at the product distribution facility.

In one aspect, a redirection of the product 190a from conveyor 110a to conveyor 110b and/or then to conveyor 110c is effectuated via the electronic inventory management device 180 sending a signal via the network 115 to the conveyor control unit 140a. In response to receipt of such a signal by the conveyor control unit 140a, the conveyor control unit 140a causes the redirection of the product 190 from the product advancement surface 120a of conveyor 110a to the product advancement surface 120b of conveyor 110b at the transfer node provided via transfer conveyor 130a. It will be appreciated that the redirection of the product 190a from the conveyor 110a to the conveyor 110b is effectuated, in some configurations, via a transfer conveyor control unit coupled directly to the transfer conveyor 130a, and which may receive a redirection-requiring signal either from the conveyor control unit 140a, or directly from the electronic inventory management device 180.

In some embodiments, the display screen 260 of the electronic inventory management device 180 is configured to display various graphical interface-based menus, options, and/or alerts that may be transmitted from and/or to the electronic inventory management device 180 in connection with various aspects of receiving electronic data from the sensors 150, 155, 166 and/or from the electronic database 170 and/or the routing/rerouting of the products 190a-190c on the conveyors 110a-110c. The inputs 270 of the electronic inventory management device 180 may be configured to permit an operator to navigate through the on-screen menus on the electronic inventory management device 180 and make changes and/or updates to the routes of the products 190a-190c and/or cause transfers of products 190a-190c between conveyors 110a-110c. It will be appreciated that the display screen 260 may be configured as both a display screen and an input 270 (e.g., a touch-screen that permits an operator to press on the display screen 260 to enter text and/or execute commands.)

Figure 3:
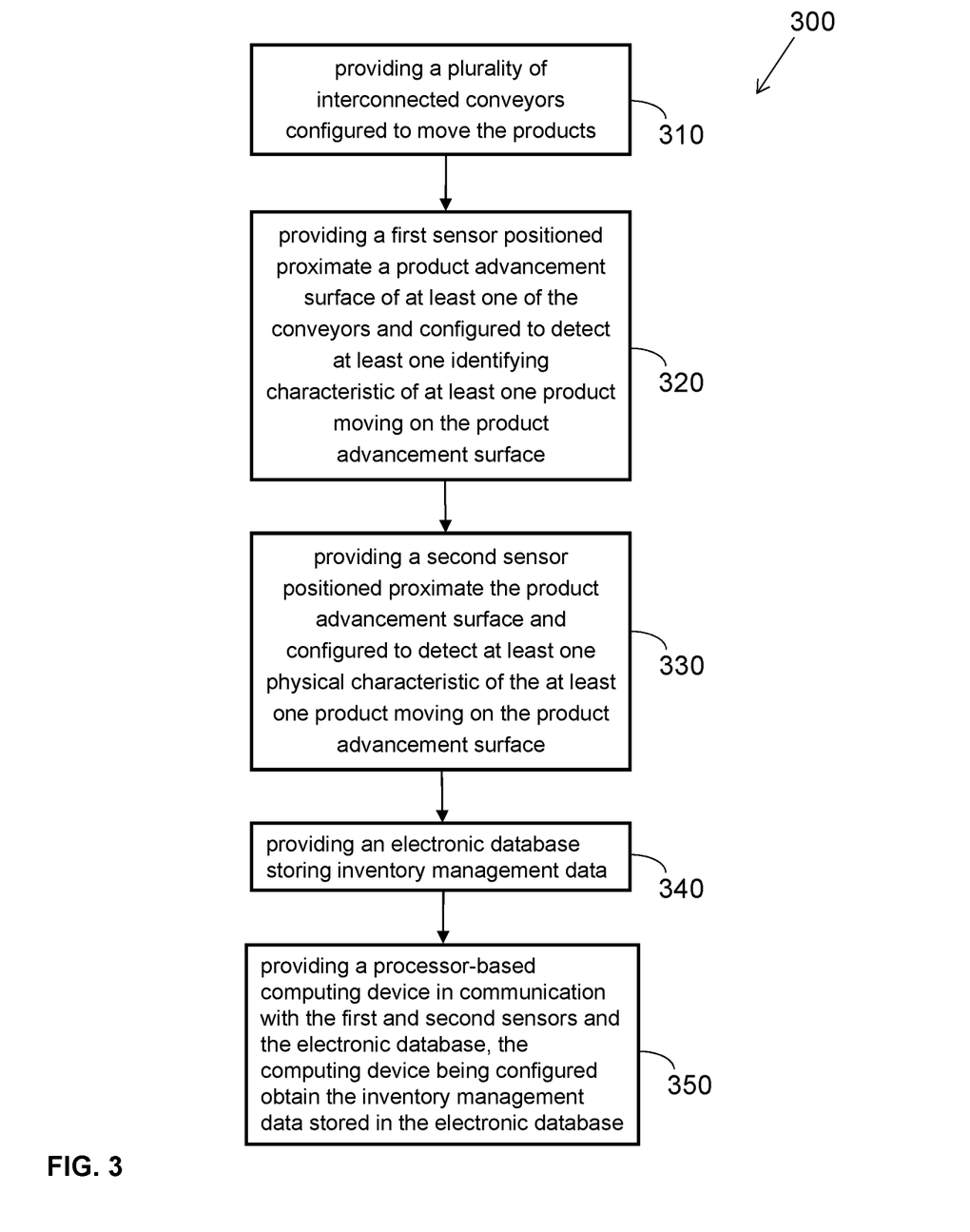
FIG. 3 is a flow chart diagram of a process of sorting and tracking products at a product distribution facility includes a plurality of interconnected conveyors configured to move the products in accordance with some embodiments.

FIG. 3 shows an embodiment of an exemplary method 300 of sorting and tracking products 190a-190c at a product distribution facility. The method 300 includes providing interconnected conveyors 110a-110c configured to move products 190a-190c (step 310). As described above, the conveyors 110a-110c of FIG. 1 can be horizontally adjacent or vertically stacked relative to one another and include one or more conveyors 130a and 130b interconnecting the conveyors 110a-110c and providing multiple transfer nodes where the products 190a-190c may be transferred between the conveyors 110a-110c. In some aspects, the conveyors 110a-110c and the transfer conveyors 130a-130b are independently movable relative to one another.

The method 300 of FIG. 3 further includes providing a first sensor 150 positioned proximate a product advancement surface 120a of at least one of the conveyors 110a and configured to detect at least one identifying characteristic of at least one product 190a moving on the product advancement surface 120a (step 320). As described above, such a sensor 150 can include but is not limited to a motion-detecting sensor, a photo sensor, a radio frequency identification (RFID) sensor, an optical sensor, a barcode sensor, and a digital camera sensor.

The method 300 of FIG. 3 further includes providing a second sensor 155 positioned proximate the product advancement surface 120a and configured to detect at least one physical characteristic of the at least one product 190a moving on the product advancement surface 120 (step 330). As described above, such a sensor 155 can include but is not limited to a weight sensor, a volumetric sensor, size sensor, a 3-D sensor, a gas/chemical sensor, an infrared sensor, a thermal sensor, or the like.

As discussed above, as the product 190a moves along the product advancement surface 120a of conveyor 110a, the product 190a is detected by the first and second sensors 150 and 155. In one aspect, the first sensor 150 detects one or more identifying characteristics associated with the product 190 (e.g., bar code, RFID, etc.) while the second sensor 155 detects one or more physical characteristics of the product 190a (e.g., size, weight, shape, temperature etc.). In some aspects, the method 300 can include providing a third sensor 160 positioned proximate the product advancement surface 120a and configured to detect a location or a presence of the product 190a moving on the product advancement surface 120a. For example, in one aspect, the third sensor 160 is a motion-detecting sensor that detects the presence of the product 190a on the product advancement surface 120a and activates (either directly, or via the electronic inventory management device 180) one or more of the first and second sensors 150 and 155 in order to facilitate the scanning of the identifying and physical characteristics of the product 190a.

As discussed above, the electronic data obtained by the sensors 150, 155, and 160 is transmitted over the network 115 to an electronic database 170 for storage and is available for retrieval by the electronic inventory management device 180. To that end, the exemplary method 300 of FIG. 3 includes providing an electronic database 170 for storing inventory management data (step 340). As described above, the exemplary electronic database 170 stores electronic data associated with the products 190a-190c moving on the conveyors 110a-110c, which includes but is not limited to data that indicates: one or more predefined identifying characteristics associated with the products 190a-190c; one or more predefined physical characteristic associated with the products 190a-190c; actual identifying characteristic information associated with the products 190a-190c; and actual physical characteristic information associated with the products 190a-190c.

As explained above, the actual identifying characteristic (e.g., barcode, RFID, etc.) information stored in the electronic database corresponds to electronic data acquired by the sensor 150 upon scanning the products 190a-190c and transmitted by the sensor 150 to the electronic database 170 over the network 115. Similarly, the actual physical characteristic (e.g., weight, size, shape, temperature etc.) information stored in the electronic database 170 corresponds to electronic data acquired by the sensor 155 upon scanning the products 190a-190c and transmitted by the sensor 155 to the electronic database 170 over the network 115. The predefined identifying characteristic associated with the products 190a-190c stored in the electronic database 170 corresponds to an electronic identifier complementary to the RFID, barcode, or other identifier present on the products 190a-190c. The predefined physical characteristic associated with the products 190a-190c stored in the electronic database 170 corresponds to default physical characteristics (e.g., weight, size, shape, temperature) of the products 190a-190c when they are in a new and undamaged conditions and/or at their desired or required storage temperature (e.g., to preserve freshness or desired shape). In some aspects the predefined physical characteristics associated with the products 190a-190c stored in the electronic database 170 also include tolerated thresholds (e.g., percentages, degrees, etc.) that, if exceeded, would result in an error signal in association with a product 190a and/or cause the product 190a to be diverted from conveyors 110a to conveyor 110b (e.g., for returning to the product sorting area, for disposal, etc.).

The method 300 of FIG. 3 further includes providing a processor-based electronic inventory management device 180 in communication with the first sensor 150, second sensor 155, and electronic database 170 and configured obtain the inventory management data stored in the electronic database 170 (step 350). In some aspects, based on the inventory management data obtained from the electronic database 170 in association with the products 190a-190c, the electronic inventory management device 180 compares the data indicating the actual identifying characteristic information associated with the products 190a-190c detected by the sensor 150 during movement of the products 190a-190c on the product advancement surface 120a-120c to the data indicating the predefined identifying characteristic information associated with the products 190a-190c in order to determine an identity of the product 190a detected by the sensor 150. In other aspects, based on the inventory management data obtained from the electronic database 170 in association with the products 190a-190c, the electronic inventory management device 180 compares the data indicating the actual physical characteristic information associated with the products 190a-190c detected by the sensor 155 during movement of the products 190a-190c on the product advancement surface 120a-120c—to the data indicating the predefined physical characteristic information associated with the products 190a-190c in order to verify that the identity and physical condition of the products 190a-190c detected by the sensor 155 reflect new and undamaged products 190a-190c at appropriate storage temperatures.

As described above, if the aforementioned comparison of the actual identifying and physical characteristic to the predefined identifying and physical characteristic by the electronic inventory management device 180 results in a determination, by the electronic inventory management device 180, that a verification of the identity of the product 190a failed, or that the product 190a is not in a new condition, or that the products 190a is in a damaged condition, or that the products 190a is not being transported at a temperature suitable to maintain the freshness or physical integrity of the product 190a, to generate an electronic error message. Such an electronic error message can be transmitted by the electronic inventory management device 180 over the network 115 to the electronic database 170 to create an error record, or to an electronic device of a worker at the product distribution facility to prompt the worker to take action. In some embodiments, if a verification of the identity of the product 190a failed, or if the product 190a is not in a new condition, or if the product 190a is in a damaged condition, or if the product 190a is not being transported at a temperature required for storing this product 190a, the electronic inventory management device 180 redirects movement of the product 190a on the product advancement surface 120a of the conveyor 110a. In some aspects, a redirection of the product 190a can be effectuated via the electronic inventory management device 180 sending a signal via the network 115 to the conveyor control unit 140a, and the conveyor control unit 140a, in response to receipt of such a signal, causing the redirection of the product 190a from the product advancement surface 120a of conveyor 110a to the product advancement surface 120b of conveyor 110b at a transfer node provided by the transfer conveyor 130a.

In some embodiments, the data obtained by a weight sensor 155 is analyzed by the electronic inventory management device 180 not only to detect physical anomalies (e.g., damage, spillage, etc.) associated with a product 190a, but also to facilitate product packing optimization. For example, in one aspect, a product 190a that is interpreted by the control circuit 210 of the electronic inventory management device 180 as heavy item (i.e., because it exceeds a certain preset heavy item threshold, for example, 20 pounds, 50 pounds, 100 pounds, etc.) can be directed by the electronic inventory management device 180 along the product advancement surface 120a of the conveyor 110a directly to loading, which facilitates the loading of the heavy items first (i.e., at a bottom of a stack). In another aspect, the control circuit 210 of the electronic inventory management device 180 is programmed to temporarily divert products 190a that are not considered heavy items from conveyor 110a to a bypass conveyor (e.g., 110b) in order to allow the heavy items to pass first and arrive first at the output point of conveyor 110a to be loaded at a bottom of a stack, then to transfer the lighter items back to conveyor 110a and permit the light items to continue traveling on conveyor 110a to the output point, thereby facilitating the workers at the product distribution facility in loading the heavier products 190a first and the lighter products 190a on top of the heavy products 190.

In some embodiments, an error condition associated with an inappropriate temperature of a product 190a sensed by a thermal/infrared sensor 155 results in an optimizing redirection of the product 190a from conveyor 110a to conveyor 110b for transporting to a cold area. Such a redirection expedites the transporting of the temperature-sensitive product 190a along the conveyor 110a to a delivery truck having a frozen and/or a refrigerated section. Such expediting is effectuated, in some aspects, by temporarily diverting, via a signal generated by the control circuit 210 of the electronic inventory management device 180, products 190a that are not temperature-sensitive from conveyor 110a to a bypass conveyor (e.g., 110b) in order to allow the temperature-sensitive products 190a to pass first and arrive first at the output point of conveyor 110a to be loaded into a frozen or refrigerated section of a delivery vehicle, then to transfer the non-temperature-sensitive products 190a back to conveyor 110a and permit the non-temperature-sensitive products 190a to continue traveling on conveyor 110a to the output point, thereby reducing the travel time on the conveyor 110*a* for temperature-sensitive products 190*a*.

In some embodiments, the data obtained by a 3-D sensor 155 is analyzed by the electronic inventory management device 180 not only to detect physical anomalies (e.g., damage, spillage, deformation, etc.) associated with a product 190*a*, but also to facilitate product packing optimization. For example, in one aspect, a product 190*a* that is interpreted by the control circuit 210 of the electronic inventory management device 180 as a large-sized item (i.e., because it exceeds a certain preset large item threshold) can be directed by the electronic inventory management device 180 along the product advancement surface 120*a* of the conveyor 110*a* directly to loading, which facilitates the loading of the largest items first (i.e., at a bottom of a stack). In another aspect, the control circuit 210 of the electronic inventory management device 180 is programmed to temporarily divert products 190*a* that are considered small-sized items from conveyor 110*a* to a bypass conveyor (e.g., 110*b*) in order to allow the larger items to pass first and arrive first at the output point of conveyor 110*a* to be loaded at a bottom of a stack, then to transfer the smaller-sized items back to conveyor 110*a* and permit the smaller-sized items to continue traveling on conveyor 110*a* to the output point, thereby facilitating the workers at the product distribution facility in loading the larger-sized products 190*a* first and the smaller-sized products 190*a* on top of the larger-sized products 190.

The systems and methods described herein advantageously include multiple conveyors for transporting products and multiple sensors configured to track and identify the products moving on the conveyors, as well as to detect any damage, undesired storage condition, or another anomaly associated with the products. The anomalies detected by the sensors in association with the products are analyzed by an electronic inventory management device, which can redirect the products on the conveyors back to a staging area, where the products can be evaluated and/or repackaged and/or disposed, thereby advantageously preventing products that are damaged or otherwise unsuited for use by the consumers from being delivered to the consumers. Accordingly, the methods and systems described herein advantageously reduce product returns by customers and thereby increase customer happiness and loyalty relative to the retailers and result in significant time and cost savings for product distribution facility operators.

Those skilled in the art will recognize that a wide variety of other modifications, alterations, and combinations can also be made with respect to the above described embodiments without departing from the scope of the invention, and that such modifications, alterations, and combinations are to be viewed as being within the ambit of the inventive concept.

What is claimed is:

1. A system for sorting and tracking products at a product distribution facility, the system comprising:
    a plurality of interconnected conveyors configured to move the products;
    a first sensor positioned proximate a product advancement surface of at least one of the conveyors and configured to detect at least one identifying characteristic of at least one product moving on the product advancement surface;
    a second sensor positioned proximate the product advancement surface and configured to detect at least one physical characteristic of the at least one product moving on the product advancement surface;
    an electronic database storing inventory management data including:
        data indicating predefined identifying characteristic and physical characteristic information associated with the at least one product, the predefined identifying characteristic and physical characteristic information corresponding to the at least one product when in a new condition and undamaged; and
        data indicating actual identifying characteristic information associated with the at least one product, the actual identifying characteristic information corresponding to the at least one product when detected by the first sensor during movement of the at least one product along the product advancement surface;
        data indicating actual physical characteristic information associated with the at least one product, the actual physical characteristic information corresponding to the at least one product when detected by the second sensor during movement of the at least one product along the product advancement surface;
    a third sensor positioned proximate the product advancement surface and configured to detect a location of the at least one product moving on the product advancement surface; and
    a processor-based electronic inventory management device in communication with the first and second sensors and the electronic database, the electronic inventory management device being configured obtain the inventory management data stored in the electronic database and, based on the obtained inventory management data, to:
        compare the data indicating the actual identifying characteristic information associated with the at least one product detected by the first sensor during movement on the product advancement surface to the data indicating the predefined identifying characteristic information associated with the at least one product in order to determine an identity of the at least one product detected by the first sensor;
        compare the data indicating the actual physical characteristic information associated with the at least one product detected by the second sensor during movement on the product advancement surface to the data indicating the predefined physical characteristic information associated with the at least one product in order to verify that the identity of the at least one product and that the condition of the at least one product detected by the second sensor is new and undamaged; and
        redirect movement of the at least one product detected by the first and second sensors on the product advancement surface of the at least one of the conveyors in response to a determination, by the electronic inventory management device, that a verification of the identity of the at least one product failed or that the at least one product is not in a new condition or is in a damaged condition;
    wherein the inventory management data stored in the electronic database further includes data indicating predefined route information associated with the at least one product; and
    wherein the electronic inventory management device is configured to compare actual route information of the at least one product based on detection of the at least one product by the third sensor to the predefined route information associated with the at least one product in the electronic database in order to determine whether the actual route of the at least one product moving on the product advancement surface of the at least one of the conveyors is consistent with the predefined route information associated with the at least one product.

2. The system of claim 1, wherein the first sensor includes at least one of a motion-detecting sensor, a photo sensor, a radio frequency identification (RFID) sensor, an optical sensor, a barcode sensor, and a digital camera sensor.

3. The system of claim 1, wherein the second sensor includes at least one of a weight sensor, a volumetric sensor, and a size sensor.

4. The system of claim 1, further comprising a control unit coupled to the conveyors and configured to control directional movement of the conveyors, wherein the electronic inventory management device is configured, in response to a successful verification of the identity of the at least one product and that the at least one product is in a new and undamaged condition, to transmit a signal to the control unit to cause the control unit to permit the at least one product to continue moving on the product advancement surface of the at least one of the conveyors without being redirected.

5. The system of claim 1, wherein the electronic inventory management device is configured, in response to a determination, by the electronic inventory management device, that a verification of the identity of the at least one product failed or that the at least one product is not in a new condition or is in a damaged condition, to transmit an electronic error message to an electronic device of a worker at the product distribution facility.

6. The system of claim 1, wherein the electronic inventory management device, is configured, in response to a determination by the electronic inventory management device that the actual route of the at least one product moving on the product advancement surface of the at least one of the conveyors is inconsistent with the predefined route information associated with the at least one product in the electronic database, to redirect movement of the at least one product along the product advancement surface onto a path consistent with the predefined route information associated with the at least one product.

7. The system of claim 6, further comprising a plurality of transfer nodes interconnecting the plurality of conveyors, each of the transfer nodes configured to permit transfer of the at least one product between the product advancement surface of one of the conveyors and the product advancement surface of another one of the conveyors, and wherein the electronic inventory management device is configured to redirect the route of the at least one product onto the path consistent with the route information associated with the at least one product via at least one of the transfer nodes.

8. The system of claim 6, wherein the electronic inventory management device is configured, in response to the determination by the electronic inventory management device that the actual route of the at least one product moving on the product advancement surface of the at least one of the conveyors is inconsistent with the route information associated with the at least one product, to transmit an electronic error message to an electronic device of a worker at the product distribution facility.

9. A system for sorting and tracking products at a product distribution facility, the system comprising:
a plurality of interconnected conveyors configured to move the products;
a first sensor positioned proximate a product advancement surface of at least one of the conveyors and configured to detect at least one identifying characteristic of at least one product moving on the product advancement surface;
a second sensor positioned proximate the product advancement surface and configured to detect at least one physical characteristic of the at least one product moving on the product advancement surface;
an electronic database storing inventory management data including:
  data indicating predefined identifying characteristic and physical characteristic information associated with the at least one product, the predefined identifying characteristic and physical characteristic information corresponding to the at least one product when in a new condition and undamaged; and
  data indicating actual identifying characteristic information associated with the at least one product, the actual identifying characteristic information corresponding to the at least one product when detected by the first sensor during movement of the at least one product along the product advancement surface;
  data indicating actual physical characteristic information associated with the at least one product, the actual physical characteristic information corresponding to the at least one product when detected by the second sensor during movement of the at least one product along the product advancement surface; and
a processor-based electronic inventory management device in communication with the first and second sensors and the electronic database, the electronic inventory management device being configured obtain the inventory management data stored in the electronic database and, based on the obtained inventory management data, to:
  compare the data indicating the actual identifying characteristic information associated with the at least one product detected by the first sensor during movement on the product advancement surface to the data indicating the predefined identifying characteristic information associated with the at least one product in order to determine an identity of the at least one product detected by the first sensor;
  compare the data indicating the actual physical characteristic information associated with the at least one product detected by the second sensor during movement on the product advancement surface to the data indicating the predefined physical characteristic information associated with the at least one product in order to verify that the identity of the at least one product and that the condition of the at least one product detected by the second sensor is new and undamaged; and
  redirect movement of the at least one product detected by the first and second sensors on the product advancement surface of the at least one of the conveyors in response to a determination, by the electronic inventory management device, that a verification of the identity of the at least one product failed or that the at least one product is not in a new condition or is in a damaged condition;
wherein the electronic database further includes order information associated with the at least one product moving on the product advancement surface, and wherein the electronic inventory management device is further configured to obtain the order information associated with the at least one product from the electronic database after a successful verification by the electronic inventory management device of the identity of the at least one product and that the at least one product is in a new and undamaged condition, and to determine whether the verified identity of the at least one product moving on the product advancement surface of the at least one of the conveyors is consistent with the order information associated with the at least one product obtained by the electronic inventory management device from the electronic database.

10. A method for sorting and tracking products at a product distribution facility, the method comprising:

providing a plurality of interconnected conveyors configured to move the products;

providing a first sensor positioned proximate a product advancement surface of at least one of the conveyors and configured to detect at least one identifying characteristic of at least one product moving on the product advancement surface;

providing a second sensor positioned proximate the product advancement surface and configured to detect at least one physical characteristic of the at least one product moving on the product advancement surface;

providing a third sensor positioned proximate the product advancement surface and configured to detect a location of the at least one product moving on the product advancement surface;

providing an electronic database storing inventory management data including:

data indicating predefined identifying characteristic and physical characteristic information associated with the at least one product, the predefined identifying characteristic and physical characteristic information corresponding to the at least one product when in a new condition and undamaged; and data indicating actual identifying characteristic information associated with the at least one product, the actual identifying characteristic information corresponding to the at least one product when detected by the first sensor during movement of the at least one product along the product advancement surface;

data indicating actual physical characteristic information associated with the at least one product, the actual physical characteristic information corresponding to the at least one product when detected by the second sensor during movement of the at least one product along the product advancement surface; and providing a processor-based electronic inventory management device in communication with the first and second sensors and the electronic database, the electronic inventory management device being configured obtain the inventory management data stored in the electronic database and, based on the obtained inventory management data, to:

compare the data indicating the actual identifying characteristic information associated with the at least one product detected by the first sensor during movement on the product advancement surface to the data indicating the predefined identifying characteristic information associated with the at least one product in order to determine an identity of the at least one product detected by the first sensor;

compare the data indicating the actual physical characteristic information associated with the at least one product detected by the second sensor during movement on the product advancement surface to the data indicating the predefined physical characteristic information associated with the at least one product in order to verify that the identity of the at least one product and that the condition of the at least one product detected by the second sensor is new and undamaged; and redirect movement of the at least one product detected by the first and second sensors on the product advancement surface of the at least one of the conveyors in response to a determination, by the electronic inventory management device, that a verification of the identity of the at least one product failed or that the at least one product is not in a new condition or is in a damaged condition;

storing, on the electronic database, data indicating predefined route information associated with the at least one product; and comparing, via the electronic inventory management device actual route information of the at least one product based on detection of the at least one product by the third sensor to the predefined route information associated with the at least one product in the electronic database in order to determine whether the actual route of the at least one product moving on the product advancement surface of the at least one of the conveyors is consistent with the predefined route information associated with the at least one product.

11. The method of claim 10, wherein the first sensor includes at least one of a motion-detecting sensor, a photo sensor, a radio frequency identification (RFID) sensor, an optical sensor, a barcode sensor, and a digital camera sensor.

12. The method of claim 10, wherein the second sensor includes at least one of a weight sensor, a volumetric sensor, and a size sensor.

13. The method of claim 10, further comprising:

providing a control unit coupled to the conveyors and configured to control directional movement of the conveyors; and transmitting, via the electronic inventory management device and in response to a successful verification of the identity of the at least one product and that the at least one product is in a new and undamaged condition, a signal to the control unit to cause the control unit to permit the at least one product to continue moving on the product advancement surface of the at least one of the conveyors without being redirected.

14. The method of claim 10, further comprising transmitting, via the electronic inventory management device and in response to a determination, by the electronic inventory management device, that a verification of the identity of the at least one product failed or that the at least one product is not in a new condition or is in a damaged condition, an electronic error message to an electronic device of a worker at the product distribution facility.

15. The method of claim 10, further comprising redirecting, via the electronic inventory management device and in response to a determination by the electronic inventory management device that the actual route of the at least one product moving on the product advancement surface of the at least one of the conveyors is inconsistent with the predefined route information associated with the at least one product in the electronic database, movement of the at least one product along the product advancement surface onto a path consistent with the predefined route information associated with the at least one product.

16. The method of claim 15, further comprising:
providing a plurality of transfer nodes interconnecting the plurality of conveyors, each of the transfer nodes configured to permit transfer of the at least one product between the product advancement surface of one of the conveyors and the product advancement surface of another one of the conveyors; and
redirecting, via the electronic inventory management device, the route of the at least one product onto the path consistent with the route information associated with the at least one product via at least one of the transfer nodes.

17. The method of claim 15, further comprising transmitting, via the electronic inventory management device and in response to the determination by the electronic inventory management device that the actual route of the at least one product moving on the product advancement surface of the at least one of the conveyors is inconsistent with the route information associated with the at least one product, an electronic error message to an electronic device of a worker at the product distribution facility.

18. A method for sorting and tracking products at a product distribution facility, the method comprising:
providing a plurality of interconnected conveyors configured to move the products;
providing a first sensor positioned proximate a product advancement surface of at least one of the conveyors and configured to detect at least one identifying characteristic of at least one product moving on the product advancement surface;
providing a second sensor positioned proximate the product advancement surface and configured to detect at least one physical characteristic of the at least one product moving on the product advancement surface;
providing an electronic database storing inventory management data including:
data indicating predefined identifying characteristic and physical characteristic information associated with the at least one product, the predefined identifying characteristic and physical characteristic information corresponding to the at least one product when in a new condition and undamaged; and
data indicating actual identifying characteristic information associated with the at least one product, the actual identifying characteristic information corresponding to the at least one product when detected by the first sensor during movement of the at least one product along the product advancement surface;
data indicating actual physical characteristic information associated with the at least one product, the actual physical characteristic information corresponding to the at least one product when detected by the second sensor during movement of the at least one product along the product advancement surface; and
providing a processor-based electronic inventory management device in communication with the first and second sensors and the electronic database, the electronic inventory management device being configured obtain the inventory management data stored in the electronic database and, based on the obtained inventory management data, to:
compare the data indicating the actual identifying characteristic information associated with the at least one product detected by the first sensor during movement on the product advancement surface to the data indicating the predefined identifying characteristic information associated with the at least one product in order to determine an identity of the at least one product detected by the first sensor;
compare the data indicating the actual physical characteristic information associated with the at least one product detected by the second sensor during movement on the product advancement surface to the data indicating the predefined physical characteristic information associated with the at least one product in order to verify that the identity of the at least one product and that the condition of the at least one product detected by the second sensor is new and undamaged; and
redirect movement of the at least one product detected by the first and second sensors on the product advancement surface of the at least one of the conveyors in response to a determination, by the electronic inventory management device, that a verification of the identity of the at least one product failed or that the at least one product is not in a new condition or is in a damaged condition;
storing, on the electronic database, order information associated with the at least one product moving on the product advancement surface;
obtaining, via the electronic inventory management device, the order information associated with the at least one product from the electronic database after a successful verification by the electronic inventory management device of the identity of the at least one product and that the at least one product is in a new and undamaged condition; and
determining, via the electronic inventory management device, whether the verified identity of the at least one product moving on the product advancement surface of the at least one of the conveyors is consistent with the order information associated with the at least one product obtained by the electronic inventory management device from the electronic database.

* * * * *